United States Patent
Mahavadi et al.

(10) Patent No.: US 11,754,546 B2
(45) Date of Patent: Sep. 12, 2023

(54) METHODS AND SYSTEMS FOR CRUDE OIL BLENDING WITH QUALITY AND COMPOSITION MONITORING AND CONTROL

(71) Applicant: Schlumberger Technology Corporation, Sugar Land, TX (US)

(72) Inventors: Sharath Chandra Mahavadi, Lexington, MA (US); Ravinath Kausik Kadayam Viswanathan, Sharon, MA (US); Kamilla Fellah, Somerville, MA (US); Simon Ivar Andersen, Tikoeb (DK); Yiqiao Tang, Chongqing (CN); Yi-Qiao Song, Newton Center, MA (US); Shawn David Taylor, Reading, MA (US); Gary Potten, Spring, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 309 days.

(21) Appl. No.: 16/954,512

(22) PCT Filed: Dec. 10, 2018

(86) PCT No.: PCT/US2018/064652
§ 371 (c)(1),
(2) Date: Jun. 16, 2020

(87) PCT Pub. No.: WO2019/125794
PCT Pub. Date: Jun. 27, 2019

(65) Prior Publication Data
US 2020/0340971 A1    Oct. 29, 2020

Related U.S. Application Data

(60) Provisional application No. 62/607,601, filed on Dec. 19, 2017.

(51) Int. Cl.
*G01N 33/28* (2006.01)
*C10G 7/00* (2006.01)
*G01N 24/08* (2006.01)

(52) U.S. Cl.
CPC .......... *G01N 33/2829* (2013.01); *C10G 7/00* (2013.01); *G01N 24/085* (2013.01); *C10G 2300/1033* (2013.01); *C10G 2300/302* (2013.01)

(58) Field of Classification Search
CPC ............... C10G 7/00; C10G 2300/302; C10G 2300/1033; G01N 24/085; G01N 33/2829
See application file for complete search history.

(56) References Cited

U.S. PATENT DOCUMENTS

| | | |
|---|---|---|
| 5,796,251 A | 8/1998 | Le Febre et al. |
| 2009/0004748 A1 | 1/2009 | Ganesan |

(Continued)

FOREIGN PATENT DOCUMENTS

WO    WO-0170912 A1 *    9/2001    .......... B01J 19/0006

OTHER PUBLICATIONS

Korb, et al., "Relation and Correlation between NMR Relaxation Times, Diffusion Coefficients, and Viscosity of Heavy Crude Oils", Journal of Physical Chemistry C. vol. 119, No. 43, pp. 24439-24446 (2015).

(Continued)

*Primary Examiner* — Gregory H Curran (57) ABSTRACT

Systems and methods for monitoring a crude oil blending process use nuclear magnetic resonance (NMR) sensors which investigate properties of a plurality of crude oil streams that are mixed together to form a crude oil blend. An NMR sensor is also used to investigate the properties of the crude oil blend. The investigated properties may include viscosity. Resulting determinations may be used to control (Continued)

the input streams so that the output stream meets desired criteria. Additional sensors such as spectroscopy sensors, viscometers, and densitometers may be used in conjunction with the NMR sensors.

11 Claims, 10 Drawing Sheets

(56) References Cited

U.S. PATENT DOCUMENTS

| | | |
|---|---|---|
| 2016/0115787 A1 | 4/2016 | Mostowfi et al. |
| 2017/0097293 A1 | 8/2017 | Gupta et al. |
| 2017/0248506 A1 | 8/2017 | Gupta et al. |

OTHER PUBLICATIONS

International Search Report and Written Opinion for the counterpart International patent application PCT/US2018/064652 dated Mar. 25, 2019.

International Preliminary Report on Patentability of International Patent Application No. PCT/US2018/064652 dated Jul. 2, 2020, 12 pages.

\* cited by examiner

METHODS AND SYSTEMS FOR CRUDE OIL BLENDING WITH QUALITY AND COMPOSITION MONITORING AND CONTROL

PRIORITY

This application claims priority from provisional U.S. Ser. No. 62/607,601, filed Dec. 19, 2017.

TECHNICAL FIELD

The subject disclosure relates to the blending of crude oils. More particularly, the subject disclosure relates to systems and methods for blending crude oils prior to delivery to a refinery where the blending utilizes monitoring of quality or composition.

BACKGROUND

Blending is a key aspect of preparing crude oils for transportation and sale. A crude oil may be blended with one or more solvents, diluents, or other crude oils to produce a single mixture that meets a series of specifications for transport and sale (collectively known as crude oil blending). Specifications for the final crude oil blend typically includes a number of chemical and physical properties, including but not limited to Reid Vapor Pressure, density, viscosity, sulfur content, water content, boiling point distribution, and stability with respect to the undesired precipitation of organic solids (e.g. sludge, asphaltenes, waxes). The blending of crude oils may occur at one or more locations between the point of production and the final receiving point, namely a refinery. While the completed blend will be required to meet all of the defined product specifications prior to transport and/or sale, the actual blending operation is typically monitored and controlled using a few key properties that may be monitored in real-time (i.e. on-line) or within a reasonable amount of time after sub-sampling from the blending operation (e.g. off-line sensors or on-site lab analysis). Refineries require in-coming crude oil blends to have a uniform crude quality (i.e. well mixed such that the properties are homogeneous) since the refinery unit operations are designed to operate within specified ranges for the chemical and physical properties of the crude oil input (i.e. feed stream). In practice however, homogenous blending of multiple crudes can be a challenge to achieve within operational time frames and difficult to routinely monitor throughout the blending operation using the existing technologies.

Crude oils are a mixture of hydrocarbons with various complex chemistries. The interaction between these different chemistries plays a crucial role in determining the final properties of the crude. Typically, of primary interest is the viscosity of the final blend. The blending of two or more oils that have significantly different viscosities can result in the incomplete blending of the oils within the time frame of the mixing operation. This is a concern when blending viscous heavy oils with less viscous conventional crude oils and diluents. The viscosity is fundamentally determined by the motions of the molecules within the oil. For simple fluids, the viscosity is directly related to the rotational or translational diffusion of the molecules. As the fluid becomes more complex, or more viscous, these relations also become more complex.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Systems and methods are provided for monitoring a crude oil blending process using nuclear magnetic resonance (NMR) sensors. NMR sensors are used to investigate properties of a plurality of crude oil streams that are mixed together to form a crude oil blend. An NMR sensor is also used to investigate the properties of the crude oil blend. In embodiments, the investigated properties include at least viscosity. In one aspect, the viscosity of the input crude oil streams and the output blend may be determined by finding the $T_2$ relaxation times of the respective streams and blend. In embodiments, additional sensors such as infrared spectroscopy sensors, UV-Vis spectroscopy sensors, Raman spectroscopy sensors, viscometers, and densitometers may be used in conjunction with the NMR sensors to provide additional information and/or confirmational information for properties such as viscosity, density, and water content.

In one embodiment, NMR sensors are placed in or along fluid lines that provide (input) crude oil streams to a mixing manifold and in or along a (output) fluid line exiting the mixing fluid manifold. NMR measurements such as $T_2$ distributions are made on the input streams and the output mixture. If an NMR measurement on an output mixture reveals incomplete blending of input crude oils, corrective action may be taken. The corrective action may include one or more of: increasing the time for blending, increasing the blending activity, and modifying input quantities from the multiple input streams.

Additional aspects, embodiments, objects and advantages of the disclosed methods may be understood with reference to the following detailed description taken in conjunction with the provided drawings.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show details in more detail than is necessary, the description taken with the drawings making apparent to those skilled in the art how the several forms of the subject disclosure may be embodied in practice. Furthermore, like reference numbers and designations in the various drawings indicate like elements.

In one aspect, an NMR system is utilized to simultaneously monitor the physical properties and quality of mixing of a given blend sample. When two or more crude oil samples with different chemistries and physical properties are blended, based on the viscosity and chemistry of the individual crude samples, it may take significant time to make a uniform blend. In addition, one or more crude oils in the blend composition may not mix well and could be problematic. Crude oils with different viscosities can be quantitatively differentiated using NMR. Also, quality of the mixing can be determined using the same data set as described hereinafter.

One of the keys for the success of the crude oil production is the ability to transport the produced crude. A key specification in the transportability of the crude oil is the liquid viscosity: the heavier the crude oil, the more challenging it is to transport. While there are a number of technical options for reducing viscosity to meet transportation requirements for pipelines shipment of crude oils and crude oil blends, the primary method of preparing different crudes for shipment is by blending different crude oils to defined product specifications. Blending may occur at the well-site, at a gathering facility, or various other locations prior to shipment to the final destination (e.g. refinery). Blending may even occur at the refinery to trim the oil blends to meet feed requirements for distillation. Despite the benefits of blending to meet transport and sale requirements, blending of crude oils also introduces some risk to the quality of the produced oil blend in terms of composition and stability. For example, blending of heavier crude oils that contain significant concentrations of asphaltene with diluents or conventional crude oils that contains large amounts of paraffinic hydrocarbons can lead to the precipitation of organic solids, such as asphaltenes or sludge. Blends that produce asphaltene are referred to as phase unstable, or incompatible oil blends, or other similar terms. Unstable blends can lead to deposition and/or clogging in pipelines, storage tanks, and processing equipment. Beyond overall composition, the occurrence of solids precipitation also depends on the order of blending the crude oils and the kinetics of the blending process, including the time needed to achieve complete blending (i.e. homogeneity of the oil blend chemical and physical properties). According to one aspect, this disclosure provides systems and methods of monitoring the blending process and alerting the operators of any potential issues with the completeness and stability of the blending product—i.e. the blend quality.

Considering the crude oil blending process and the associated equipment it is a challenge to execute the blending consistently and to monitor the quality of blends. In the industry, crude oil blending is typically performed using one of two basic methods, including any variations of these basic methods: in-tank blending; and in-line blending. In-tank blending is a more traditional method where different crude oils are mixed in a fixed ratio to attain targeted physical properties such as viscosity and density. The biggest challenge with this process is inhomogeneous resultant product. In-tank blends are more likely to show gradients in viscosity and density. It is hard to achieve homogeneous mixing with in-tank blending and it is relatively expensive to operate. Therefore, operators will adjust the conditions of the blending to ensure the product meets or exceeds the sale requirements. However, by often exceeding the requirements, the blend products will have a higher financial value than the stated value based on product specifications. This difference in values is referred to as blend or quality giveaway. There will be significant blend 'giveaway' for in-tank blending process. In-tank blending may work well for light crude oils; however, when crudes with significant difference in viscosity are mixed together, the agitator or mixer tend to move both the liquids around without actually blending them. As a result, it can take an extremely long time to achieve a reasonable blend in this process.

The in-line ratio blending process is often considered superior to the in-tank blending process. In-line blending involves using a manifold or similar system to bring flows of different crude oils together and blend them within the pipeline system on a continuous basis, either with a static mixer, jet mixing, or other similar pipeline mixing technology. All of these technologies utilize a high shear environment to quickly mix the individual oils into a single oil blend. The major advantages of in-line blending process is the time required to complete the blending is significantly lower than in-tank blending and the ability to monitor and control the blend process as it occurs. The result is less blend "giveaway" relatively to in-tank blending. However, the challenges include integrating an analyzer to monitor the blend quality. As in-line blending is in real time, there is no room for error, so a proper monitoring tool is required.

Figure 1:
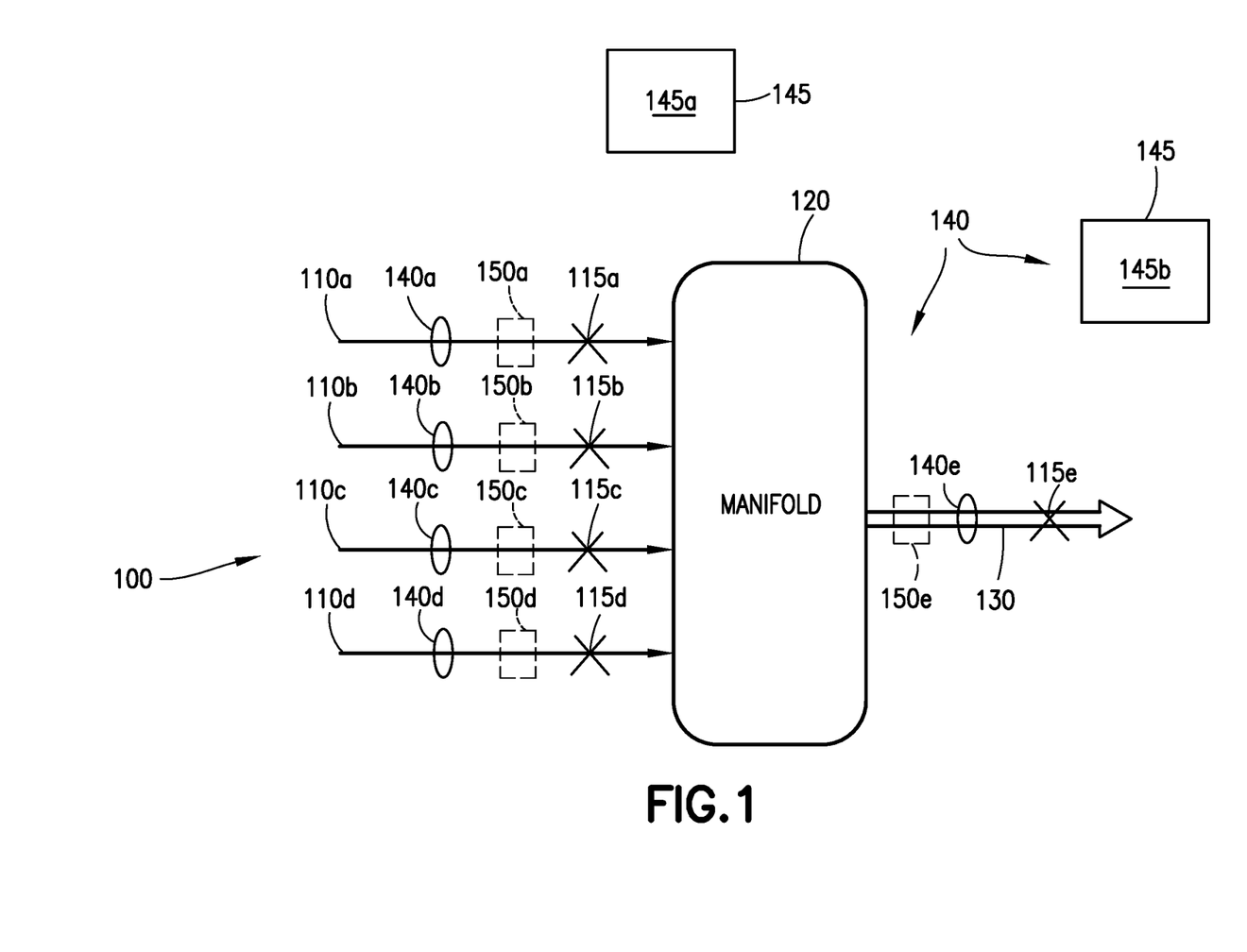
FIG. 1 is a schematic diagram of a blending system.
Figure 2A:
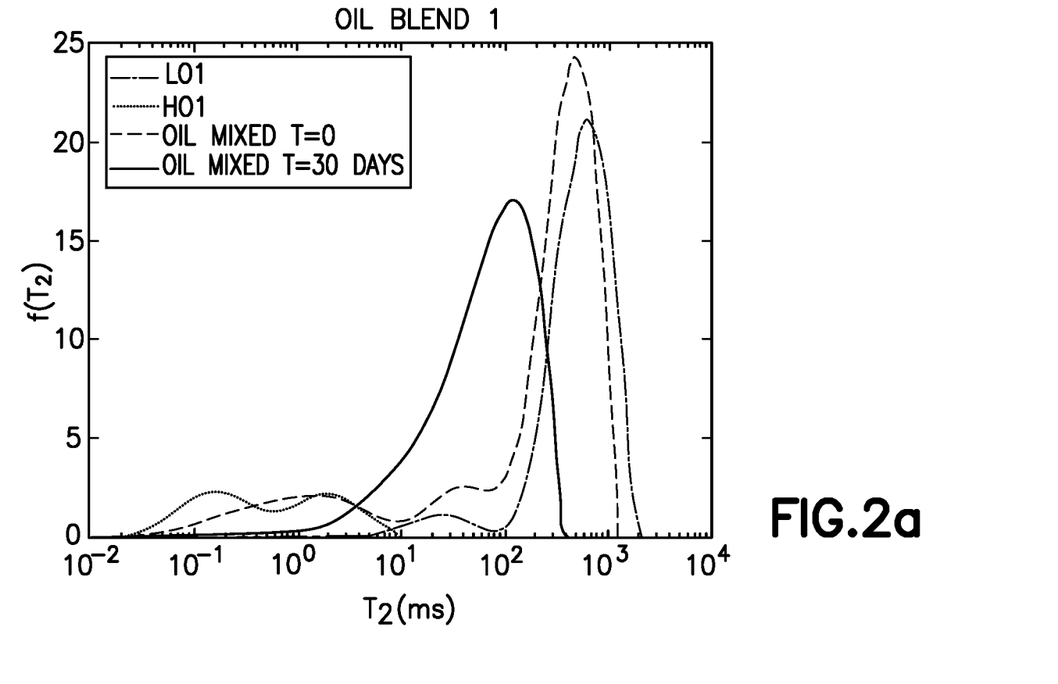
FIGS. 2a-2d are $T_2$ distribution plots of four different oil blends.
Figure 2B:
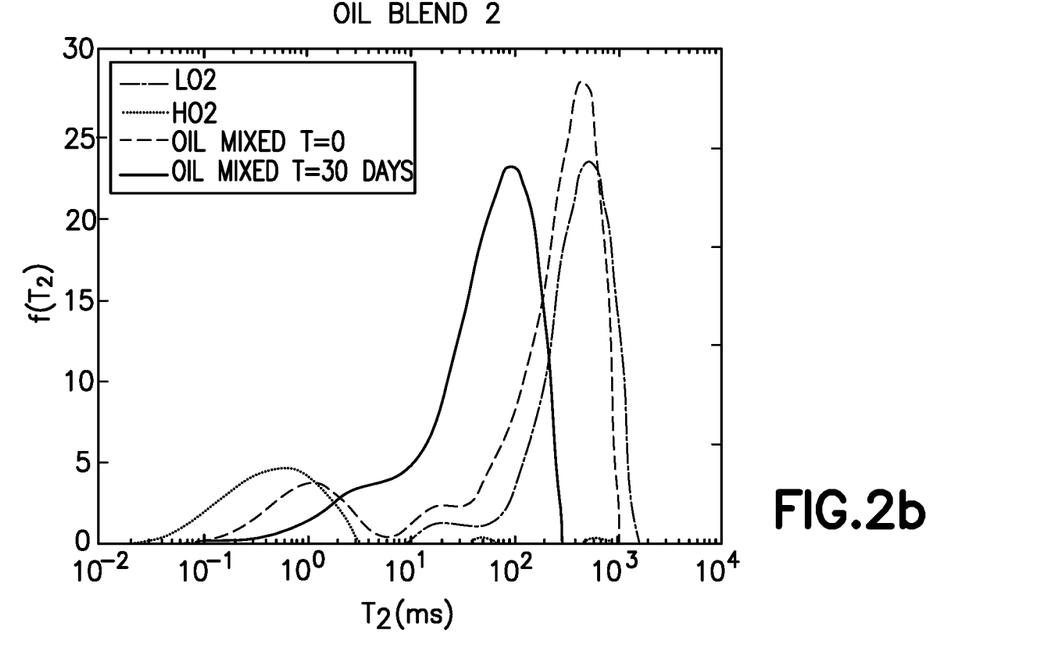
Figure 2C:
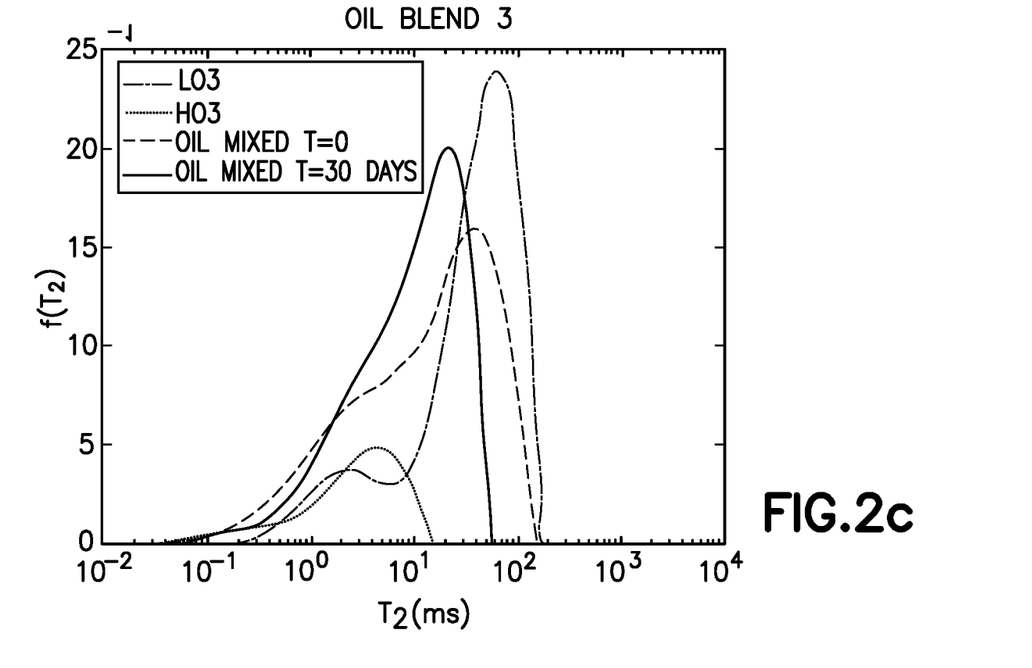
Figure 2D:
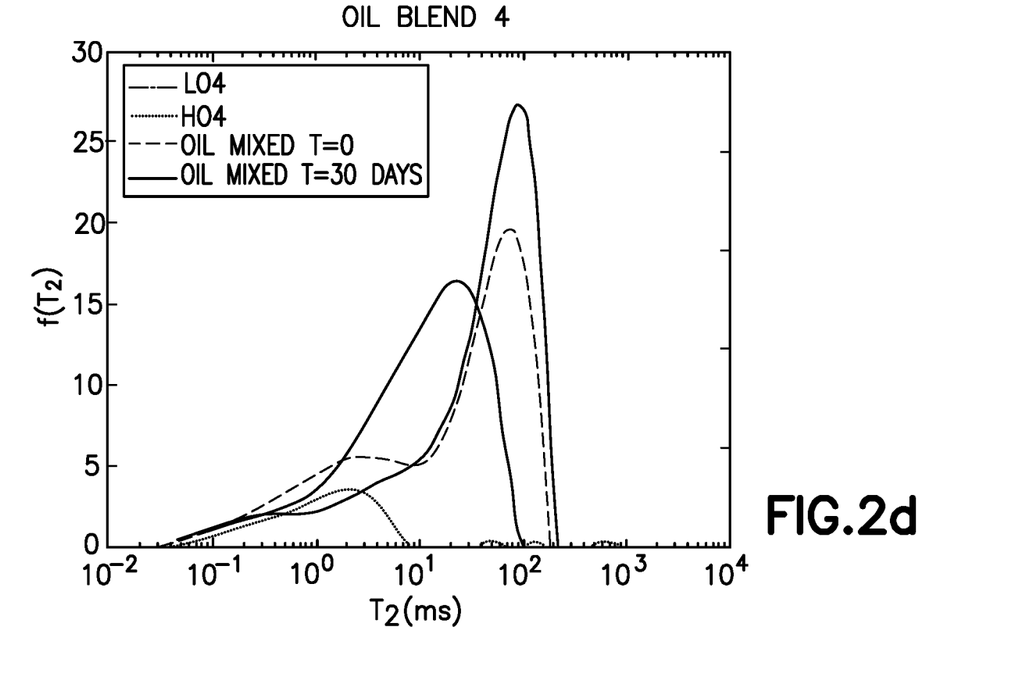

In one aspect, a solution is presented to address the aforementioned challenges and improve the existing technology for monitoring and controlling in-line blending operations. Turning to FIG. 1, a blending system 100 is shown to include a series of crude oil input lines 110a-110d, valves (control elements) 115a-115d, a mixing manifold 120, a mixed crude oil output line 130 with valve (control element) 115e, and a NMR system 140 including multiple NMR sensors 140a-140e which each include transmitters and receivers, field magnets, etc., and a computer system 145 including one or more processors or computers (two shown) 145a, 145b for processing the information obtained by the NMR sensors. The computers may be local or distant from the crude oil lines and manifold, and when multiple processors or computers are utilized, they will be connected so that information may be sent from at least all computers to a single computer. In one embodiment raw information from the sensors 140a-140e may be sent to a single computer. In another embodiment, information from the sensors may be processed locally and then sent to a single computer for analysis. In one embodiment, an NMR sensor (140a-140d) is placed in or around each input line 110a-110d, and an NMR sensor (140e) is placed in or around the output line 130. For purposes herein, an "input line" or "output line" shall be deemed to include spurs where sampling may be done. In one embodiment, the NMR system 140 detects the $T_2$ and/or $T_1$ relaxation times or distributions of the crude oil of each input line and the mixed crude oil of the output line and the processors 145a, 145b are used to relate the resulting NMR determinations to the viscosity of the crude oil in each line. See Korb, J-P, et al., "Relation and Correlation between NMR Relaxation Times, Diffusion Coefficients, and Viscosity of Heavy Crude Oils", *J. Phys Chem. C.* 119 (43) pp. 24439-24446 (2015).

In one embodiment, the computer system 145 may be coupled to and be used to control the valves 115a-115e.

In one embodiment, additional sensors 150a-150e such as infrared spectroscopy sensors, UV-Vis spectroscopy sensors, Raman spectroscopy sensors, viscometers, and densitometers may be used in conjunction with the NMR sensors 140a-140e to provide additional information and/or confirmational information for properties such as viscosity, density, and water content.

In one embodiment, electronic and/or paper printouts of information determined by the computer system are generated on a screen or on paper (not shown). By way of example only, the viscosity of the output stream may be shown as a function of time in log format.

When two or more fluid samples with different viscosities are mixed together, according to one aspect, NMR may be used to determine whether any particular fluid sample is failing to completely participate in the blend, and if so, quantitatively how much of that fluid is failing to blend. In addition, by monitoring the rate of blending for individual fluids, an estimate can be obtained as to how long it will take to complete the blending process to obtain a desired blending quality. The same estimate can also indicate which fluids are blending well and which are challenging. This would help the operator to make a decision on setting the flow rates for various fluid streams.

In FIGS. 2a-2d four examples are seen which are useful in understanding the blending process between lighter and heavier crude oils. In particular, $T_2$ distributions using NMR equipment were obtained for multiple crude oil pairs of different viscosities, separately, when mixed together into a sample container (t=0) and permitted to mix (blend) by molecular diffusion only. The viscosities of the different crude oil pairs used for the blending were significantly different. For FIG. 2a, the viscosities of the lighter and heavier crude oils were respectively LO1=5 cP, HO1=40000 cP; for FIG. 2b, the respective viscosities were LO2=5 cP, HO2=140000 cP; for FIG. 2c, the respective viscosities were LO3=50 cP, HO3=100 cP; and for FIG. 2d, the respective viscosities were LO4=20 cP, and HO4=14000 cP. As seen in all four cases, the $T_2$ distributions at the beginning of the blending process in the nonequilibrium state (t=0) can be well differentiated from the final blended equilibrium states (t=30 days in FIGS. 2a, 2b, 2c, and t=25 days in FIG. 2d). In all four cases, the $T_2$ distribution peak in the equilibrium state was between the $T_2$ peaks of the respective oils measured separately, and shorter than the $T_2$ peak measured at t=0.

In order to analyze the NMR data for this purpose, a simple model may be used to explain the evolution of mean $T_2$ over the course of fluid mixture. If no chemical reaction takes place, the process can be described by molecular diffusion. For a fluid species with diffusion coefficient D, the mean squared displacement (msd) $\langle (r(t)-r_0)^2 \rangle$ in three-dimensional space is determined by $\langle (r(t)-r_0)^2 \rangle = 6Dt$, where r(t) is the position of the particle at time t and $r_0$ is its initial position. In one aspect, it may be assumed that the time-dependent mean $T_2$ relates to the time derivative of the msd of the diffusive molecules such that when msd changes rapidly, so does $T_2$. Over time, the change of msd slows down, and accordingly $T_2(t)$ approaches a constant. Tentatively, the following formula is suggested:

$$T_2(t) \sim \frac{\partial \sqrt{\langle (r(t)-r_0)^2 \rangle}}{\partial t} \sim \frac{1}{\sqrt{t}} \qquad (1)$$

However, the above formula diverges at t=0. To address this issue, a constant, $t_0$, may be introduced, and accordingly, equation (1) may be modified:

$$T_2(t) \sim 1/\sqrt{t+t_0} \qquad (2)$$

The constant $t_0$ is a characteristic time determined by the diffusion property of the fluids.

The evolution of the arithmetic mean $T_2$ starts at $T_2(0)$ and stabilizes at $T_2(\infty)$. Utilizing equations (1) and (2), the following scaling law may be used to describe $T_2(t)$:

$$T_2(t) = \frac{T_2(0) - T_2(\infty)}{\sqrt{1 + \frac{t}{t_0}}} + T_2(\infty) \qquad (3)$$

The more diffusive the fluids are, the smaller $t_0$ is.

Figure 3:
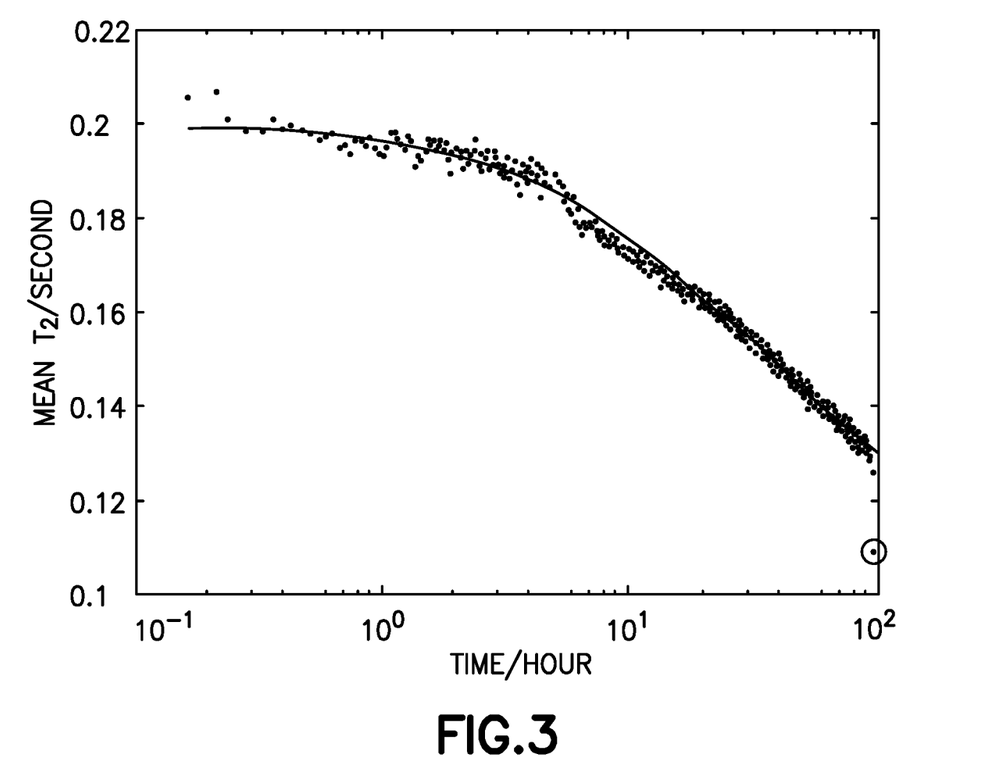
FIG. 3 is a plot of mean $T_2$ of a crude oil mixed with hexadecane as a function of mixing time in hours.

Equation (3) was used for a nonlinear fit for $T_2(t)$, with three fitting parameters; $T_2(0)$, $T_2(\infty)$, and $t_0$. FIG. 3 shows the mean $T_2$ (dots) and fitting results (line) of hexadecane mixed in the crude oil blend discussed above with reference to FIG. 2a. After 90 hours of continuous monitoring on $T_2$ of the fluid mixture, the sample was further mixed by vigorously shaking it up and down about one hundred times. As seen in FIG. 3, after shaking, the mean $T_2$ drops from 0.126 second to 0.109 second (shown by the circled dot). Although not shown, that reduced mean $T_2$ remained unchanged after a week. It should be appreciated that the curve in FIG. 2a which shows the blend after 30 days provides a result $T_2$(30 days)=$T_2(\infty)$=0.104 second. This is close to the measured $T_2$ after shaking.

It is noted that different scaling laws may be applied, depending on the extent of fluid mixing. When fluids of different composition are nearing a complete homogeneous mixture, an exponential function (derived from Fick's law) may be more appropriate to describe the change of fluid mean $T_2$ as a function of time.

Figure 4:
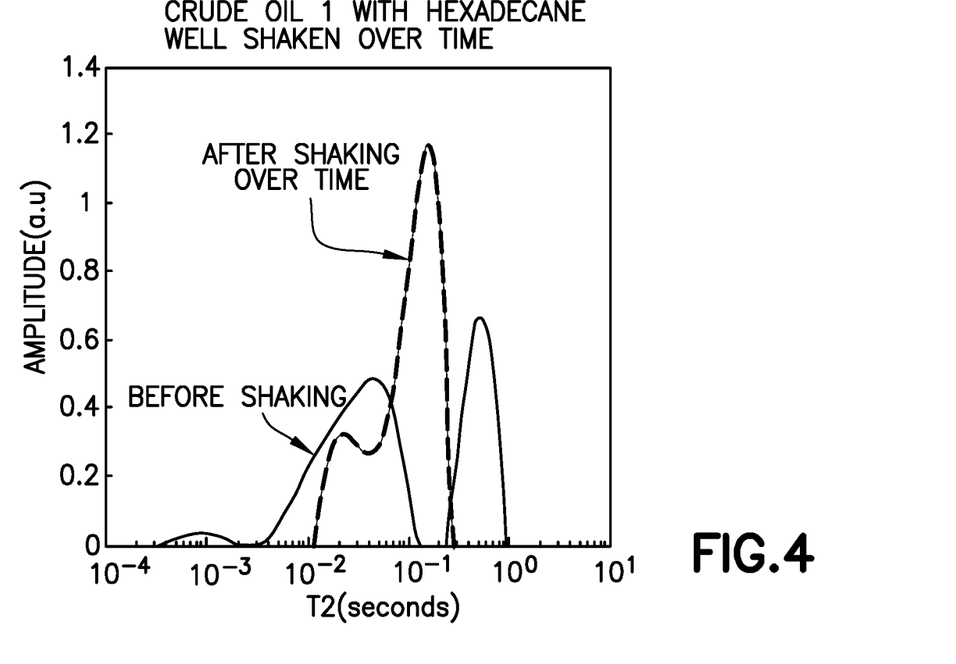
FIG. 4 is a $T_2$ distribution plot of crude oil mixed with hexadecane before and after vigorous shaking.
Figure 5:
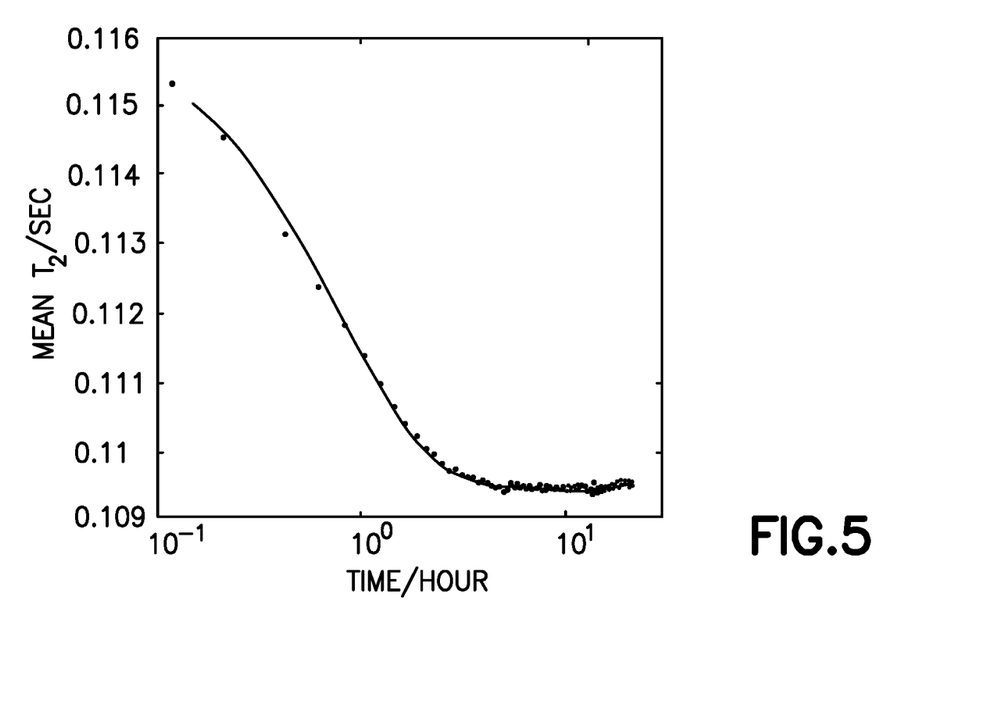
FIG. 5 is a plot of log mean $T_2$ as a function of time after vigorous shaking.
Figure 6A:
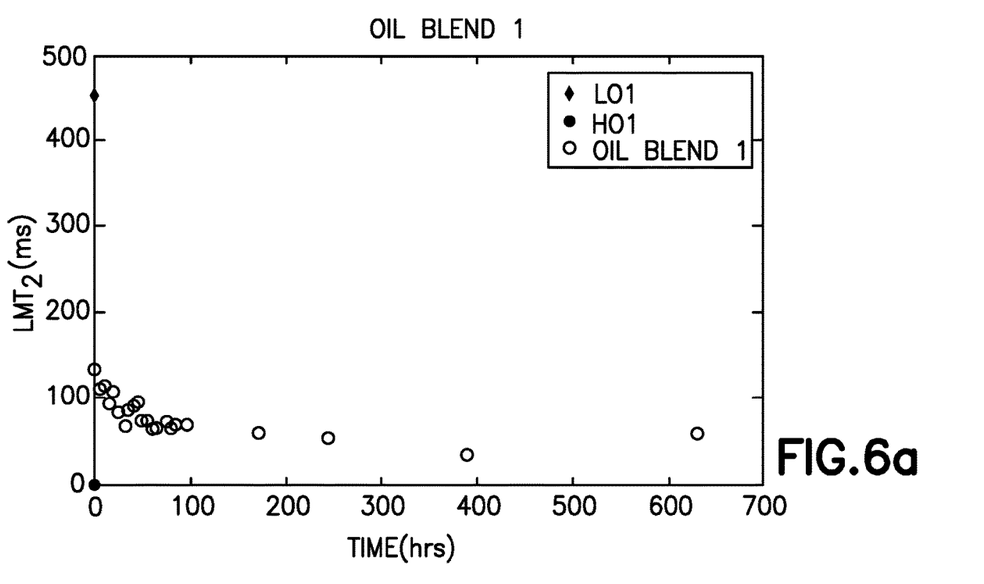
FIGS. 6a-6d are plots of log mean $T_2$ as a function of time for four blended oils.
Figure 6B:
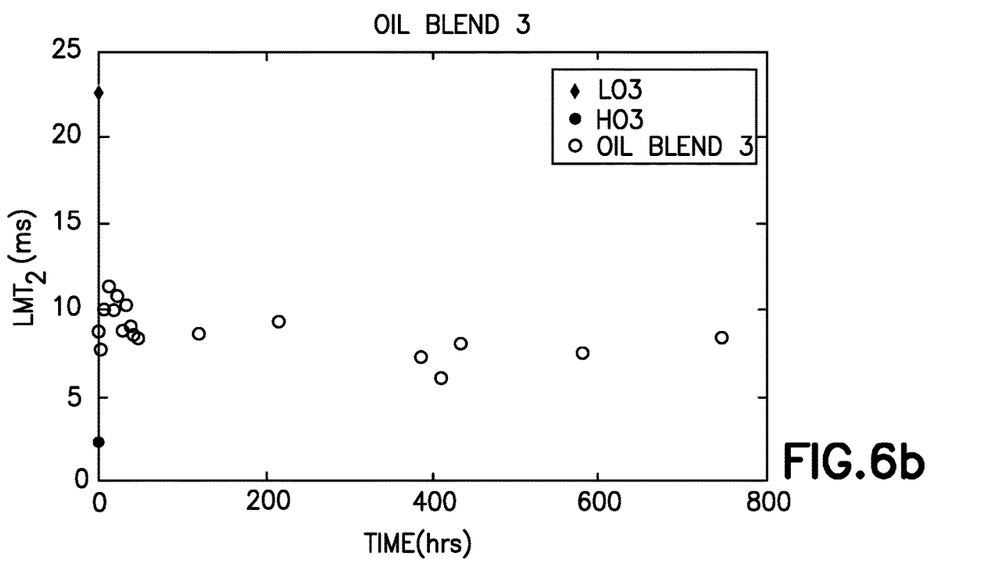
Figure 6C:
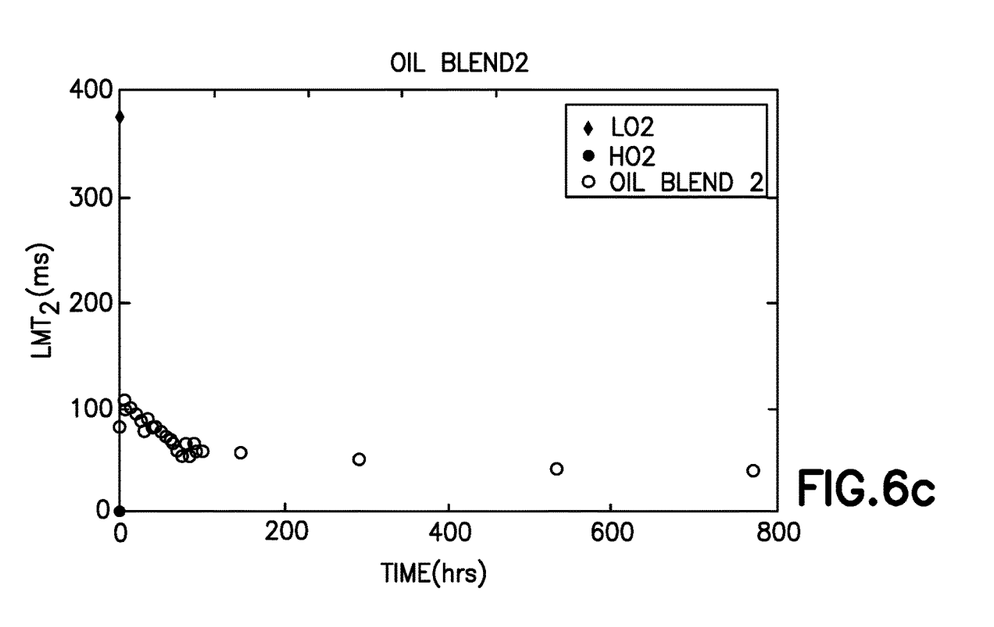
Figure 6D:
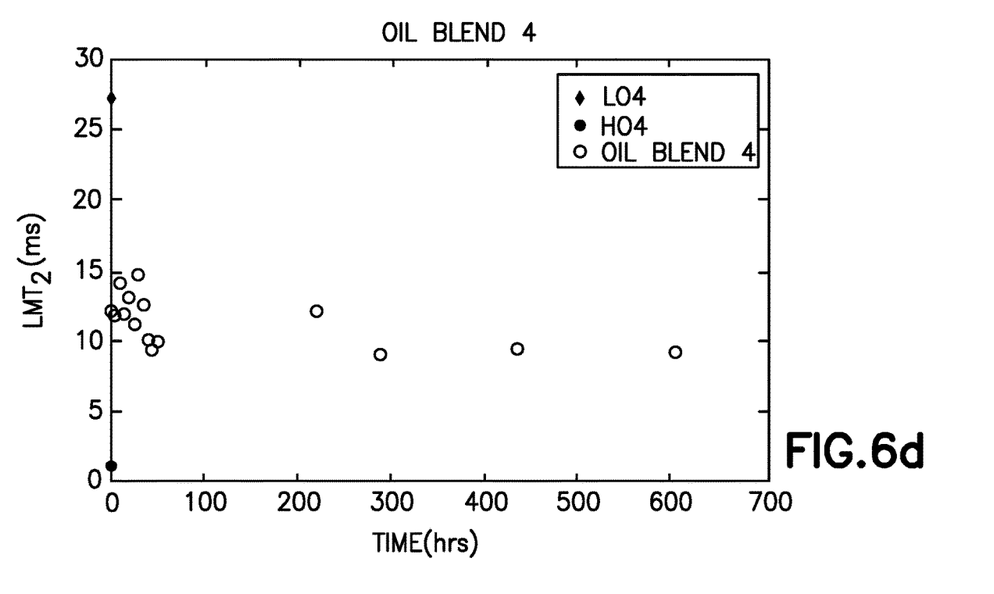

Turning to FIG. 4, the $T_2$ distribution of a crude oil with hexadecane is shown before shaking and after vigorous shaking. FIG. 5 shows measurements of the mean $T_2$ for a day after the vigorous shaking. As seen in FIG. 5, a drop of approximately 5 ms (0.005 sec) in mean $T_2$ over a course of 3 hours is observed before reaching full stabilization. Although a slight temperature change may cause the $T_2$ reduction, it is unlikely as it should reach temperature equilibrium within half an hour.

In one aspect, an exponential kernel was applied to fit the data of FIG. 5:

$$T_2(t) = (T_2(0) - T_2(\infty)) \times e^{-t/t_0} + T_2(\infty) \qquad (4)$$

where $T_2(0)$ and $T_2(\infty)$ are the initial and final $T_2$ value, and t is the mixing time. While equation (3) fits data very well, the exponential kernel of equation (4) may provide better results when describing a mixing process where different fluid components are sufficiently blended.

A similar analysis was performed on the mixture of crude oil samples (from FIGS. 2a-2d) as shown in FIGS. 6a-6d. FIGS. 6a-6d indicate how NMR log mean $T_2$ values of the blends stabilize to an average value between that of the individual components. This information can help in determining when equilibrium is attained and can be used to obtain a desired blend viscosity.

In one embodiment, besides mean $T_2$, other properties of the obtained NMR spectra may be used to quantify blending quality. One measure, which for purposes herein is called a "blending quality index" (BQI), may be used to quantify similarities among NMR spectra obtained at different time stamps which may in turn be used to track the thoroughness of fluid mixing.

According to embodiments, the spectra similarity may be quantified in different manners. One such manner is using the Bhattacharyya distance ($D_B$). Mathematically, $D_B$ can be calculated according to:

$$D_B(sp_1, sp_2) = -\ln(\Sigma \operatorname{sqrt}(sp_1 * sp_2)), \quad (5)$$

where $sp_1$ and $sp_2$ are two normalized NMR $T_2$ spectra, the symbol * indicates element-wise multiplication, and ln is a natural log operation. As will be appreciated from equation (5), when $sp_1 = sp_2$, $D_B = 0$; and conversely, the larger the difference becomes between the two spectra, the larger $D_B$ becomes.

If a well-mixed sample is available with NMR spectra $sp_0$, the blending quality index BQI is defined at time t as:

$$BQI(t) = 1 - D_B(sp(t), sp_0) / D_B(sp(t=0), sp_0). \quad (6)$$

Figure 7A:
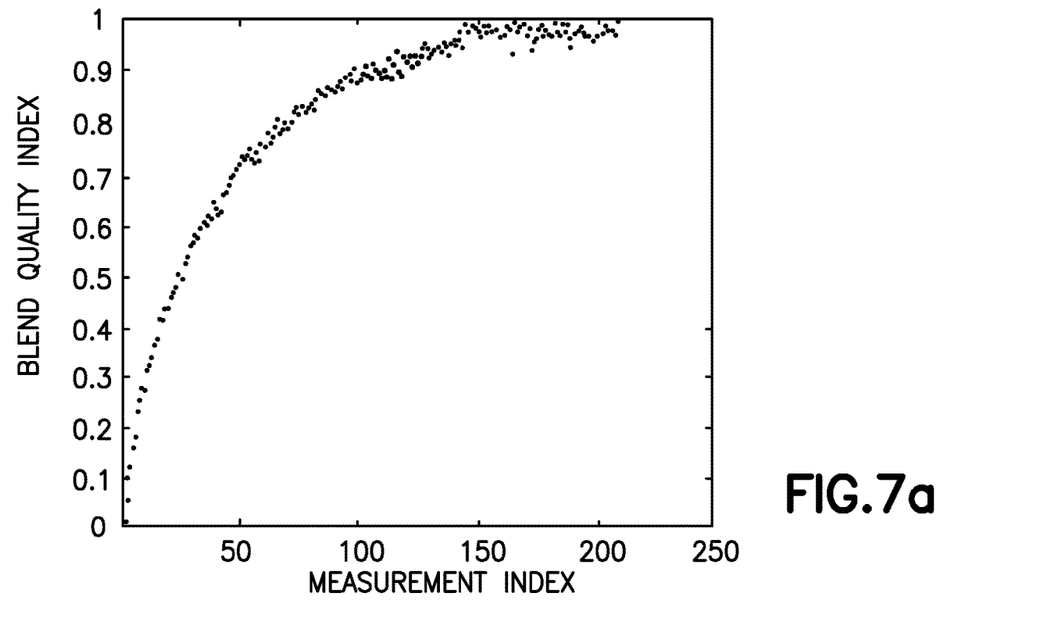
FIGS. 7a and 7b are plots of a blend quality index as a function of time for two different fluid mixtures.
Figure 7B:
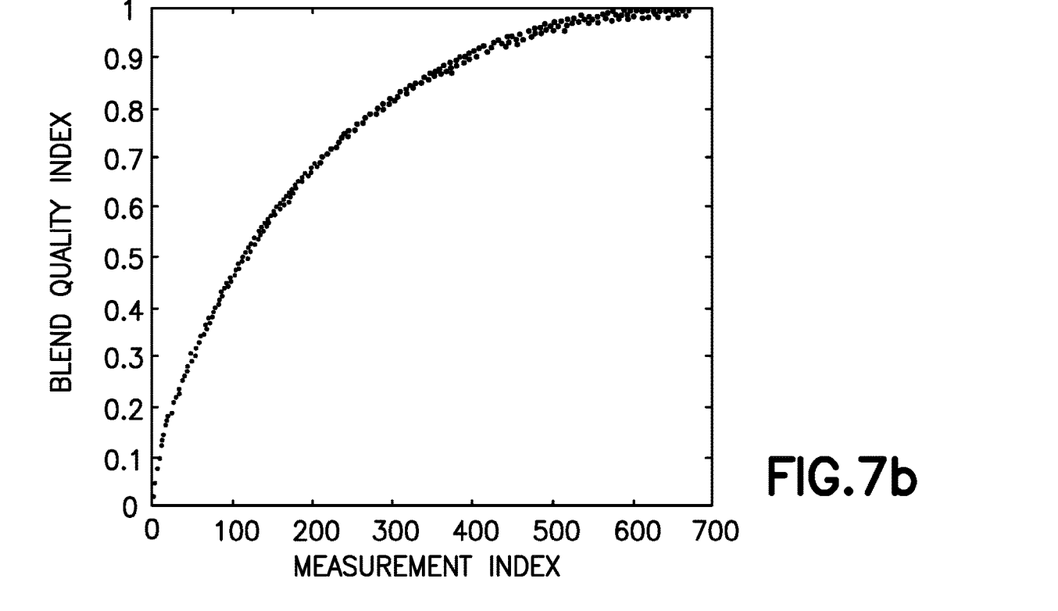

As seen in FIGS. 7a and 7b, where the BQI of two different fluid mixtures is plotted relative to a measurement index (with measurements taken at a fixed time interval), the BQI ranges from 0 to 1, with 0 being the initial fluid mix and 1 being a complete or thorough mixture. Also, as seen in FIGS. 7a and 7b, the BQI quantity increases monotonically as a function of time.

When a well-mixed sample is unavailable, the BQI is defined at time t as:

$$BQI(t) = \Sigma D_B(sp(t), sp(t-1)). \quad (7)$$

Here, BQI is a monotonically increasing function, with the rate of change slowing down over time. In this case, a first-order derivative of the quantity (d BQI/dt) may be used as a measure for gauging prospective benefits of continuing to blend the fluid mix.

According to one aspect, by using NMR sensors for analyzing the input stream and the blended stream, more efficient blend designs can be prepared with much lower cost. According to another aspect, NMR equipment may be coupled with spectroscopy equipment to obtain additional information on the physical properties and chemistry of the final blend. While the NMR equipment can provide various physical properties as indicated earlier, spectroscopy data can provide blend compositional information such as H/C ratio, aromaticity, TAN (Total acid number), total base number (TBN) etc.

According to one embodiment, using the NMR sensors and optionally the spectroscopy or other sensors, the quality of the individual crude oil streams is monitored. Quality may be monitored for viscosity and for other properties. If the quality of a crude oil stream changes such that the quality of the outgoing blend will change and/or perhaps not meet requirements, a notice or alarm may be generated by the computer system to notify the operator of the change.

According to one embodiment, using the NMR sensor on the blended output, the blend quality of the blended output is monitored. If the quality of a blended crude oil stream output changes such that the quality does not meet requirements, a notice or alarm may be generated by the computer system to notify the operator of the change. In addition, a valve on the output may be used to divert the flow as desired.

According to one embodiment, the blending of the crude oil streams is monitored using the output blended stream sensor. By way of example, if the $T_2$ distribution of the blended output provides a smooth curve (as shown for the t=30 day curve of FIG. 2a), complete blending is assumed. Conversely, if the $T_2$ distribution of the blended output shows a bumpy curve (as shown for the t=30 day curve of FIG. 2b) incomplete blending is assumed. In one embodiment, if incomplete blending is found, the $T_2$ distributions of the input streams are analyzed to identify which stream or streams may be blending completely. Once the stream or streams that is not blending completely is identified, the relative contributions of the input streams may be modified by partially or completely closing the input valves to reduce or eliminate the offending stream(s), and the input amounts may be reconfigured to obtain the desired blended output. Alternatively, if incomplete blending is found, a determination may be made whether additional mixing is required (such as sending the blended stream through an additional mixing manifold) to reduce the mean $T_2$ as suggested in FIG. 3, and/or whether additional time is required to accomplish complete blending (as suggested in FIGS. 6a-6e). Where additional time is required, the output flow may be diverted to a longer flow path.

According to one embodiment, based on the NMR measurements made on the input streams, a determination is made as to the time required for post-manifold blending. The blended crude oil may then be directed to a pipeline of desired length that provides a desired time between mixing and delivery to a refinery.

According to another embodiment, instead of using a mixing manifold, a mixing tank is used, and batches of blended crude are generated. With knowledge of the characteristics of the input crude oils obtained using NMR sensors and estimates of the kinetics of the mixing which is dependent on the chemistry and viscosity of the input crude oils, the time required to mix the crude oils in-tank in order to provide a sufficiently blended output may be estimated.

According to embodiments, by providing additional sensors such as infrared spectroscopy sensors, UV-Vis spectroscopy sensors, Raman spectroscopy sensors, viscometers, and densitometers, contaminants in the individual input crudes and in the resulting output blended crude may be identified. If the contaminants are beyond an acceptable range, the makeup of the blended crude may be modified by changing the amounts of the different input crude oils. This may be accomplished automatically and/or remotely by directing the input valves to partially or completely open or close. Similarly, the water content of the input streams and the blended output may be identified, and if beyond an acceptable range, the makeup of the blended crude may be modified by changing the amounts of the different input crude oils. Again, this may be accomplished automatically and/or remotely by directing the input valves to partially or completely open or close. Also, asphaltene fallout resulting from the blending of incompatible fluids may be detected. If so, the makeup of the blended crude may be modified by changing the amounts of the different input crude oils in order to eliminate asphaltene fallout. Again, this may be accomplished automatically and/or remotely by directing the input valves to partially or completely open or close. It is noted that the additional sensors may also be used to conduct an investigation of the incoming streams and/or the blended stream to perform viscosity estimates that may be used to confirm and/or modify the determinations made by the NMR system.

In one aspect, all the NMR or NMR and spectrometer sensors may be used to passively monitor the process or to actively monitor and control the blending operation. In an active monitor and control mode, information from the sensors would be part of a feedback control loop used to adjust the composition of the blend by varying the proportion of crude oils in the feed stream, either through changes in pump rates, valve positions, or other similar means of controlling the flow rates of the individual crude oil feed streams.

It will be appreciated that using the systems previously described, individual input crudes can be tested for their composition, properties such as viscosity, density, total acid number (TAN), total base number (TBN) etc. and for potential contaminants before qualifying for blending. In addition, once qualified, each individual fluid can be analyzed for its compatibility with the other input fluids, including the stability and quality of the expected final blend. On the output side, the final blend may be tested for its quality and stability. Based on the results, decisions can be made to either proceed with the ratio of the input streams, or to re-adjust the individual fluids ratio in the blend or to remove one or more fluids from the blend. Once the blend composition is finalized it may be analyzed for properties such as viscosity, density, total acid number (TAN), total base number (TBN), water content etc. before the final custody transfer or transferring to refinery.

Figure 8:
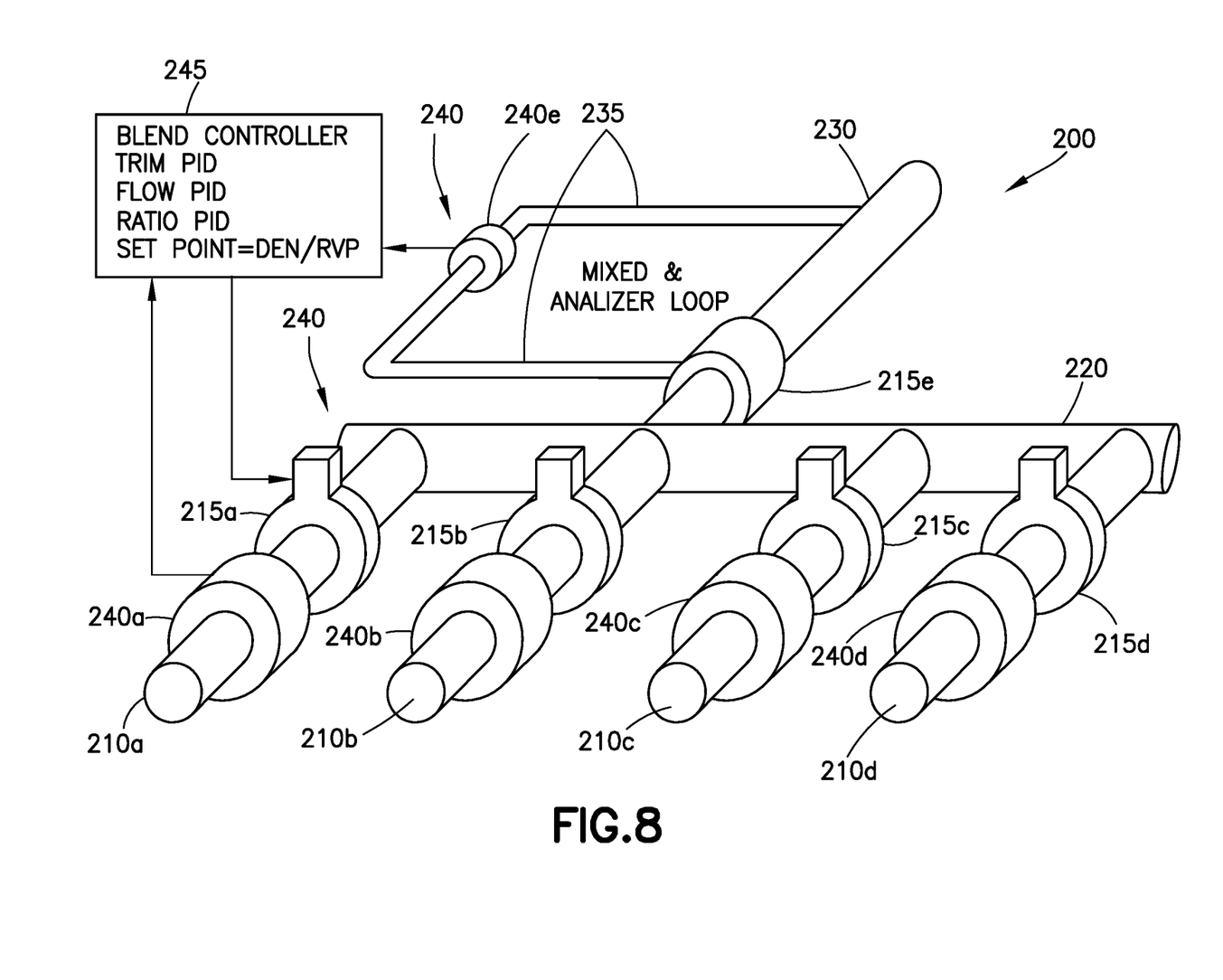
FIG. 8 is a schematic diagram of an alternative blending system.

Turning now to FIG. 8, a blending system 200 is shown to include a series of crude oil input lines 210a-210d, valves (control elements) 215a-215d, a mixing manifold 220, a mixed crude oil output line 230, an output analyzer loop 235 with valve (control element) 215e, and a NMR system 240 including multiple NMR sensors 240a-240e which each include transmitters and receivers, field magnets, etc., and a computer system 245 including one or more processors or computers (one shown) for processing the information obtained by the NMR sensors. The computer system may be local or distant from the crude oil lines and manifold, and when multiple processors or computers are utilized, they will be connected so that information may be sent from at least all computers to a single computer. In one embodiment raw information from the sensors 240a-240e may be sent to a single computer. In another embodiment, information from the sensors may be processed locally and then sent to a single computer for analysis. In one embodiment, an NMR sensor (240a-240d) is placed in or around each input line 210a-210d, and an NMR sensor (240e) is placed in or around the output analyzer loop line 235. In one embodiment, the NMR system 240 detects the $T_2$ and/or $T_1$ relaxation times or distributions of the crude oil of each input line and the mixed crude oil of the output line and the processors 245a, 245b are used to relate the resulting NMR determinations to the viscosity of the crude oil in each line. See Korb, J-P, et al., "Relation and Correlation between NMR Relaxation Times, Diffusion Coefficients, and Viscosity of Heavy Crude Oils", *J. Phys Chem. C.* 119 (43) pp. 24439-24446 (2015).

In one embodiment, the computer system 245 may be coupled to and be used to control the valves 215a-215e.

In one embodiment, additional sensors such as infrared spectroscopy sensors, UV-Vis spectroscopy sensors, Raman spectroscopy sensors, viscometers, and densitometers (not shown) may be used in conjunction with the NMR sensors 240a-240e to provide additional information and/or confirmational information for properties such as viscosity, density, and water content.

Figure 9:
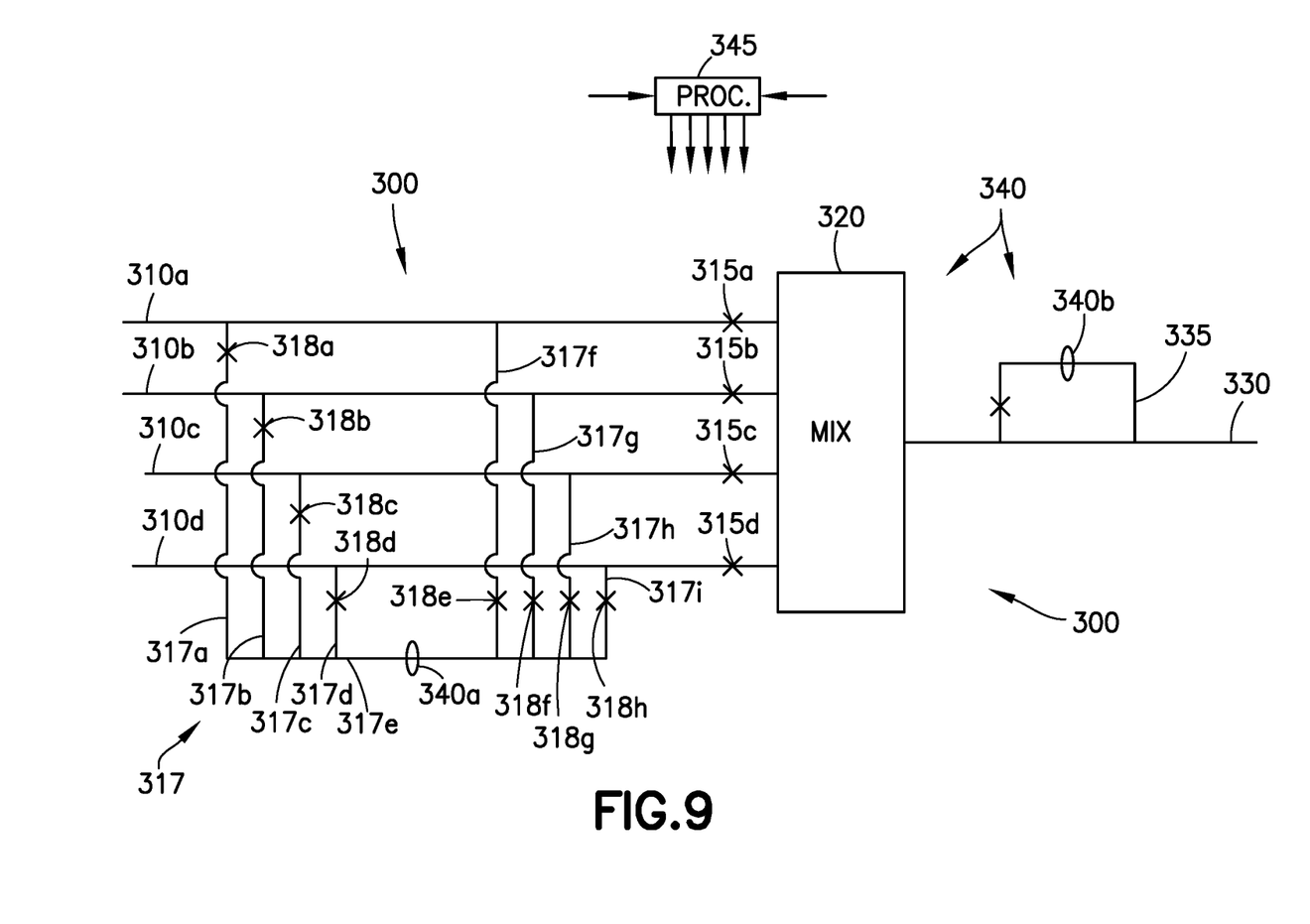
FIG. 9 is a schematic diagram of another alternative blending system.

Turning now to FIG. 9, a blending system 300 is shown to include a series of crude oil input lines 310a-310d, valves (control elements) 315a-315d, an input analyzer loop line system 317 with lines 317a-317i and valves 318a-318h, a mixing manifold 320, a mixed crude oil output line 330, an output analyzer loop line 335 with valve (control element) 215e, and a NMR system 340 including NMR sensors 340a and 340b which each includes transmitters and receivers, field magnets, etc., and a computer system 345 including one or more processors or computers (one shown) for processing the information obtained by the NMR sensors. Spur lines 317a-317d of the input analyzer loop system 317 provide samples via valves 318a-318d to analyzer line 317e. Those samples are subject to testing using NMR sensor 340a and being returned to their respective crude oil input lines 310a-310d via spur lines 317f-317i via valves 318e-318h. In this manner, a single NMR sensor 340a may be used to test each of the crude oil input samples. The valve sets (318a, 318e), (318b, 318f), (318c, 318g), and (318d, 318h) may be switched hourly, or more or less often, so that samples from lines 315a-315d are sent to line 317e, sensed by NMR sensor 340a, and timely information is obtained by the computer system 345 and acted upon. The computers may be local or distant from the crude oil lines and manifold, and when multiple processors or computers are utilized, they will be connected so that information may be sent from at least all computers to a single computer. In one embodiment raw information from the sensors 340a and 340b may be sent to a single computer. In another embodiment, information from the sensors may be processed locally and then sent to a single computer for analysis. In one embodiment, the NMR system 340 detects the $T_2$ and/or $T_1$ relaxation times or distributions of the crude oil of each input line and the mixed crude oil of the output line and the processors 345 are used to relate the resulting NMR determinations to the viscosity of the crude oil in each line. See Korb, J-P, et al., "Relation and Correlation between NMR Relaxation Times, Diffusion Coefficients, and Viscosity of Heavy Crude Oils", *J. Phys Chem. C.* 119 (43) pp. 24439-24446 (2015).

In one embodiment, the computer system 345 may be coupled to and be used to control the valves 315a-315e and 317a-317i.

In one embodiment, additional sensors (not shown) such as infrared spectroscopy sensors, UV-Vis spectroscopy sensors, Raman spectroscopy sensors, viscometers, and densitometers may be used in conjunction with the NMR sensors 340a and 340b to provide additional information and/or confirmational information for properties such as viscosity, density, and water content.

In one aspect, some of the methods and processes described above are performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims. Moreover, embodiments described herein may be practiced in the absence of any element that is not specifically disclosed herein.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of blending a plurality of crude oils of different constituent makeups to obtain a blended crude oil of desired quality, comprising:
   utilizing a nuclear magnetic resonance (NMR) system having a plurality of NMR sensors and at least one processor, and a supplemental sensor including at least one of (i) infrared spectroscopy sensors, (ii) UV-Vis spectroscopy sensors, (iii) Raman spectroscopy sensors, (iv) viscometers, and (v) densitometers, to sense crude oil flowing in a plurality of individual crude oil input streams which are combined and mixed to generate a blended output stream;
   sensing said blended output stream utilizing said NMR system;
   making a first determination regarding a property of said blended crude oil;
   comparing said first determination with a desired value; and
   modifying the rate of flow of at least one of the plurality of crude oil input streams if the determination does not meet said desired value.

2. The method of claim 1, wherein:
   the property is viscosity.

3. The method of claim 2, wherein:
   said making a first determination comprises either finding a $T_2$ relaxation distribution of the output stream or a blend quality index (BQI) of the output stream in order to determine whether the blended output stream is sufficiently blended.

4. The method of claim 3, wherein:
   said making a first determination comprises converting NMR data to a viscosity value.

5. The method of claim 3, wherein:
   said modifying comprises correlating information from said $T_2$ relaxation distribution of the output stream with $T_2$ relaxation distributions of said plurality of input streams in order to identify which of said plurality of input streams is not blending appropriately and reducing the rate of flow of the identified input stream.

6. The method of claim 5, wherein:
   said reducing the flow rate comprises modifying a setting of at least one of a pump and a valve associated with the identified input stream.

7. A method of blending a plurality of crude oils of different constituent makeups to obtain a blended crude oil of desired quality, comprising:
   utilizing a nuclear magnetic resonance (NMR) system having a plurality of NMR sensors and at least one processor, and a supplemental sensor including at least one of (i) infrared spectroscopy sensors, (ii) UV-Vis spectroscopy sensors, (iii) Raman spectroscopy sensors, (iv) viscometers, and (v) densitometers, to sense crude oil flowing in a plurality of individual crude oil input streams which are combined and mixed to generate a blended output stream;
   sensing said blended output stream utilizing said NMR system and said supplemental sensor;
   making at least a first determination regarding at least a first property of said blended crude oil;
   comparing said at least first determination with at least one desired value; and
   modifying the rate of flow of at least one of the plurality of crude oil input streams if the at least one determination does not meet said desired value.

8. The method of claim 7, wherein:
   said at least a first property is viscosity.

9. The method of claim 8, wherein:
   said making at least a first determination comprises either finding a $T_2$ relaxation distribution of the output stream or a blend quality index (BQI) of the output stream in order to determine whether the blended output stream is sufficiently blended and converting NMR data to a viscosity value.

10. The method of claim 8, wherein:
    said at least a first property further comprises at least one of density, total acid number (TAN), total base number (TBN), presence of at least one defined contaminant, water content, and asphaltene precipitation.

11. A method of blending a plurality of crude oils of different constituent makeups to obtain a blended crude oil of desired quality, comprising:
    utilizing a nuclear magnetic resonance (NMR) system having a plurality of NMR sensors and at least one processor, and a supplemental sensor including at least one of (i) infrared spectroscopy sensors, (ii) UV-Vis spectroscopy sensors, (iii) Raman spectroscopy sensors, (iv) viscometers, and (v) densitometers, to sense crude oil flowing in a plurality of individual crude oil input streams which are combined and mixed to generate a blended output stream;
    sensing said blended output stream utilizing said NMR system;
    making a first determination regarding a property of said blended crude oil;
    comparing said first determination with a desired value; and
    at least one of (i) using a mixer to further blend the output stream, and (ii) increasing an expected length of time between said sensing and a delivery of said second stream to a destination by either slowing a velocity of said output stream or increasing a length of said output stream to permit said blended output stream to further blend before reaching the destination.

\* \* \* \* \*